United States Patent [19]

Nakatsukasa et al.

[11] Patent Number: 4,513,085
[45] Date of Patent: Apr. 23, 1985

[54] FUNCTIONALLY INDEPENDENT CLONING VECTORS FOR USE IN STREPTOMYCES

[75] Inventors: Walter M. Nakatsukasa; James A. Mabe, both of Indianapolis, Ind.

[73] Assignee: Eli Lilly and Company, Indianapolis, Ind.

[21] Appl. No.: 433,197

[22] Filed: Oct. 7, 1982

[51] Int. Cl.³ .................. C12N 1/20; C12N 15/00; C12N 1/00; C07H 15/12
[52] U.S. Cl. ...................... 435/253; 435/317; 435/172.3; 536/27; 935/1; 935/29; 935/75
[58] Field of Search .............. 435/172, 317, 253; 536/27

[56] References Cited

U.S. PATENT DOCUMENTS

| | | | |
|---|---|---|---|
| 4,273,875 | 6/1981 | Manis | 435/253 |
| 4,332,900 | 6/1982 | Manis et al. | 435/172 |
| 4,338,400 | 7/1982 | Manis | 435/172 |
| 4,416,994 | 11/1983 | Nakatsukasa et al. | 435/172 |

FOREIGN PATENT DOCUMENTS 2048894  12/1980  United Kingdom .

OTHER PUBLICATIONS

International Publication No. WO79/01169.
Bibb, M. et al., 1980, Nature 284:526.
Thompson, C. et al., 1980, Nature 286:525.
Thompson, J. and Cundliffe, E., 1980, J. of Bacteriology 142(2):455.
Bibb, M. et al., 1980, Developments in Industrial Microbiology 21:55.
Gray O. et al., 1980, Abstracts of the 80th Annual ASM Meeting, Paper No. H68.

Primary Examiner—Alvin E. Tanenholtz
Attorney, Agent, or Firm—Gerald V. Dahling; Arthur R. Whale

[57] ABSTRACT

The present invention discloses functionally independent selectable recombinant DNA cloning vectors for use in Streptomyces.

49 Claims, 6 Drawing Figures

Restriction Site Map of Plasmid pEL7

Figure 1:
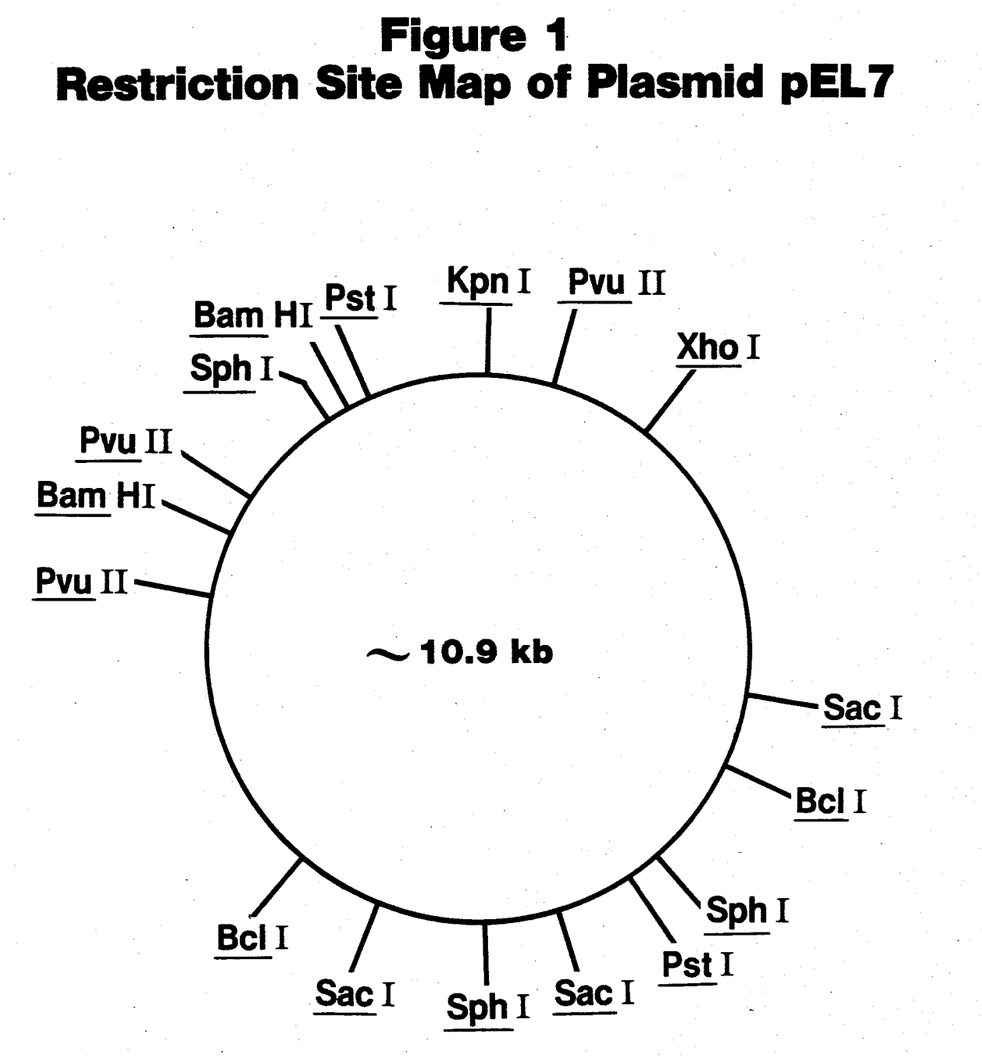

Figure 1
Restriction Site Map of Plasmid pEL7

Figure 2:
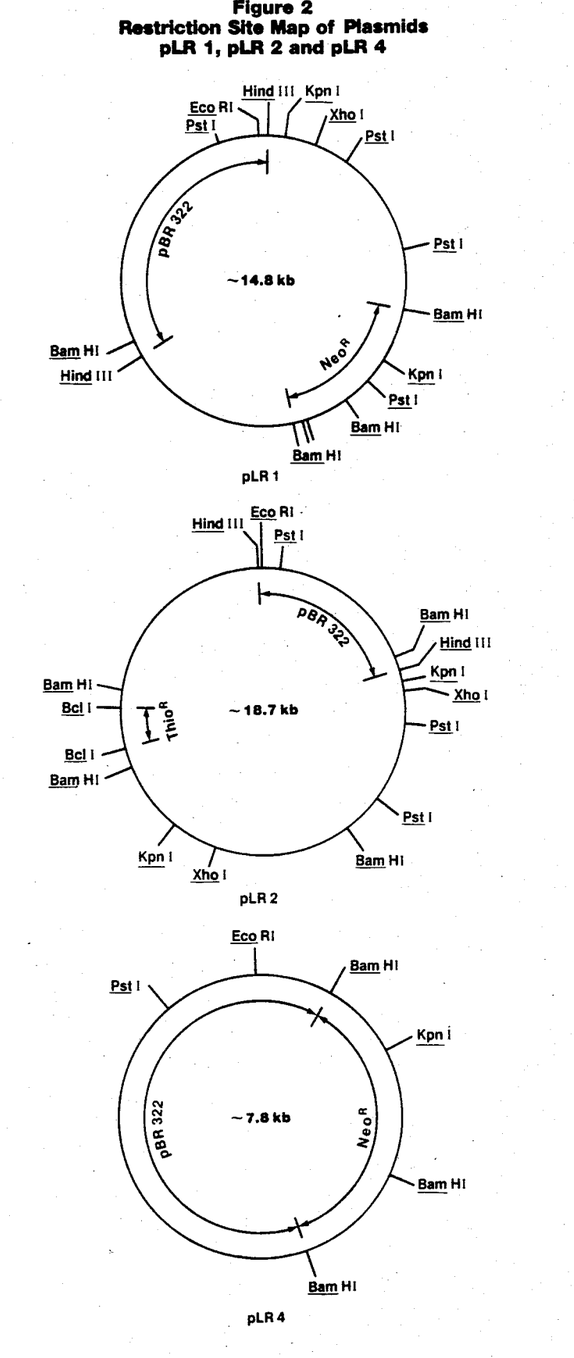

Figure 2
Restriction Site Map of Plasmids
pLR 1, pLR 2 and pLR 4

Figure 3:
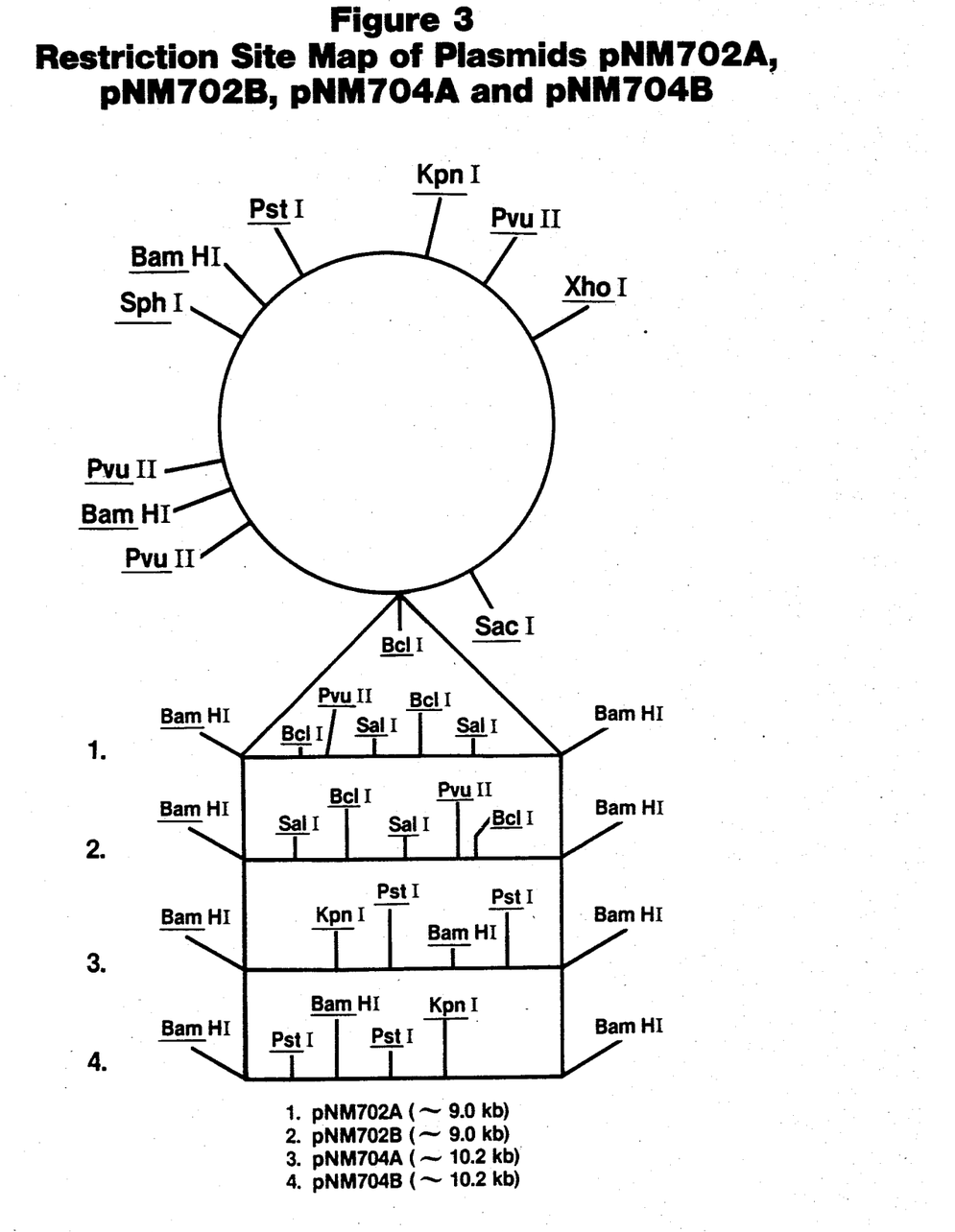

Figure 3
Restriction Site Map of Plasmids pNM702A, pNM702B, pNM704A and pNM704B 1. pNM702A (~ 9.0 kb)
2. pNM702B (~ 9.0 kb)
3. pNM704A (~ 10.2 kb)
4. pNM704B (~ 10.2 kb)

Figure 4:
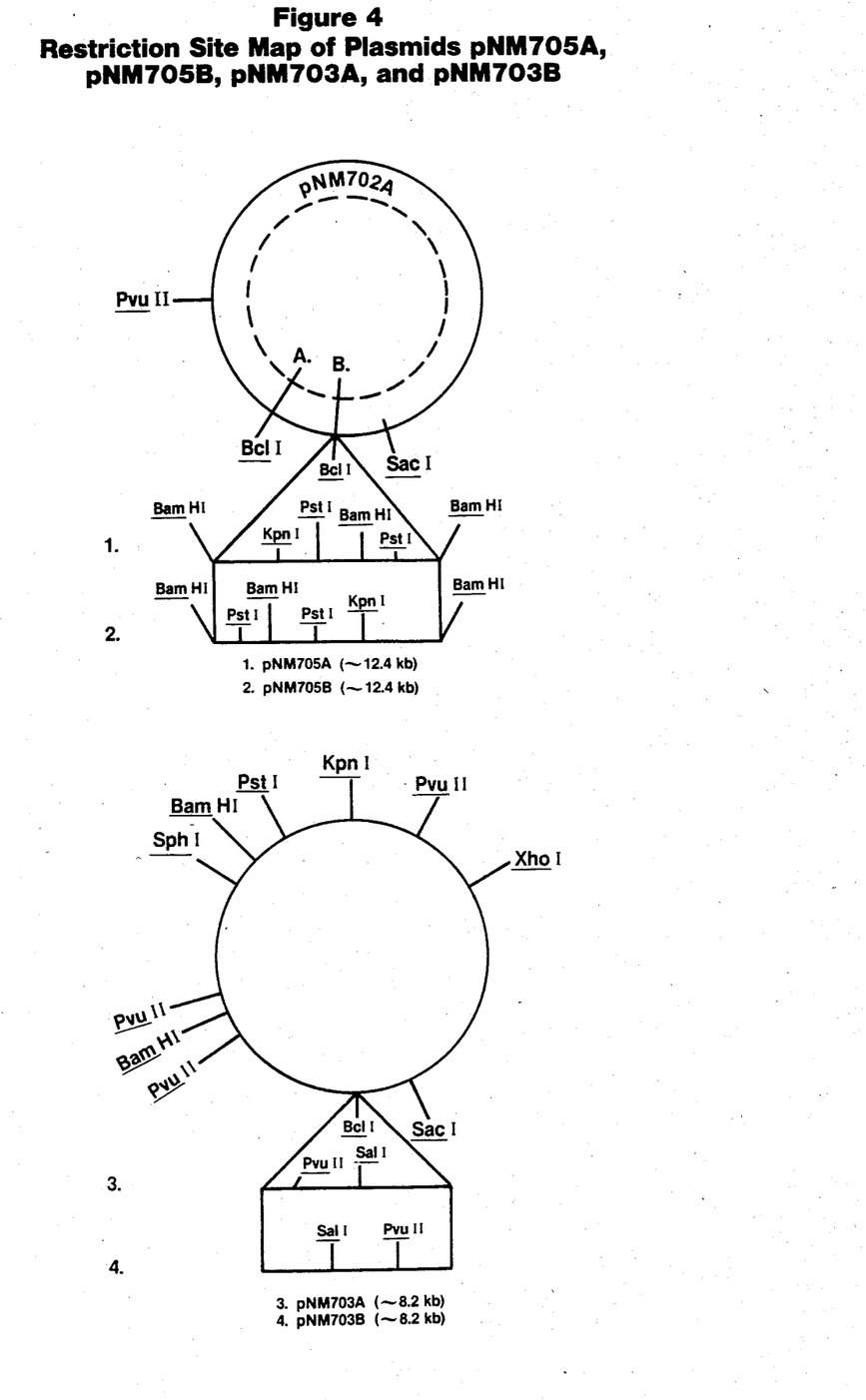

Figure 4
Restriction Site Map of Plasmids pNM705A, pNM705B, pNM703A, and pNM703B 1. pNM705A (~12.4 kb)
2. pNM705B (~12.4 kb)

3. pNM703A (~8.2 kb)
4. pNM703B (~8.2 kb)

Figure 5:
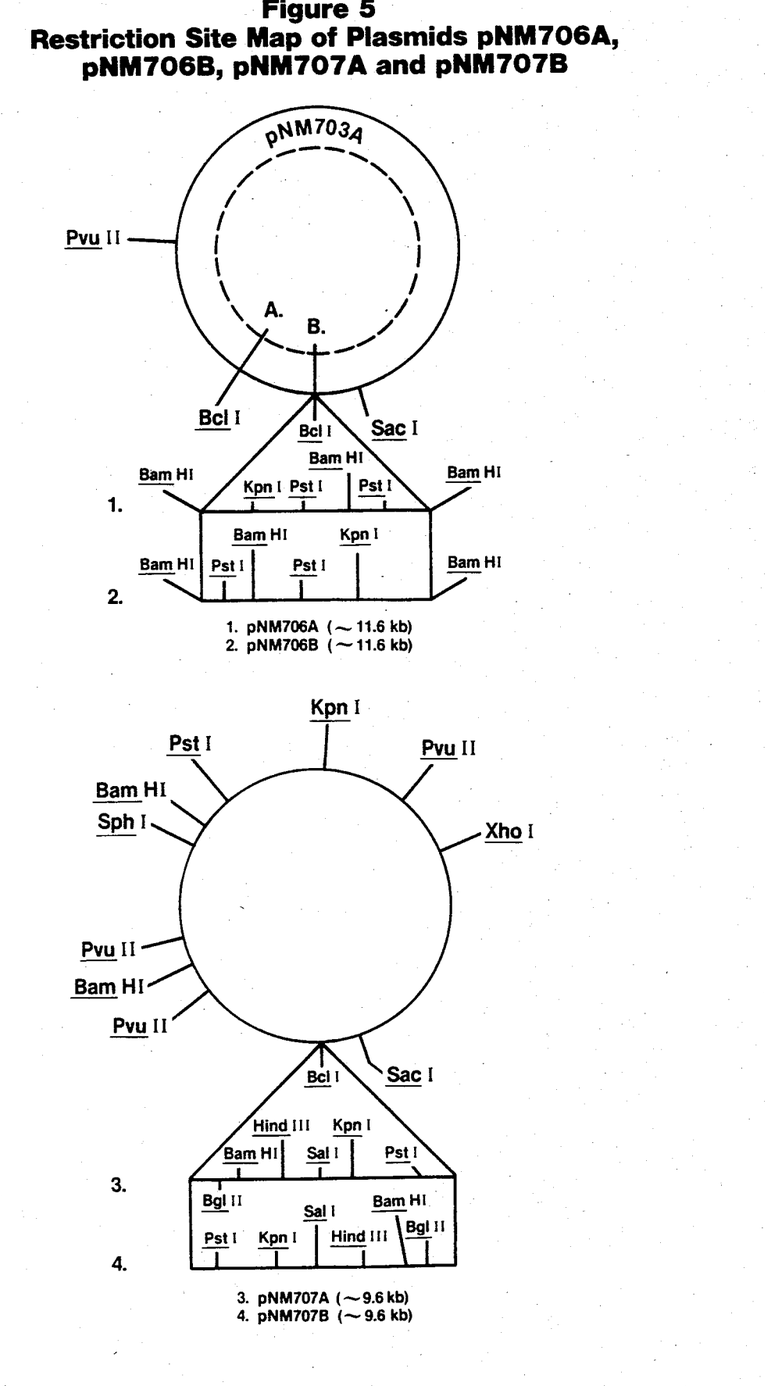

Figure 5
Restriction Site Map of Plasmids pNM706A, pNM706B, pNM707A and pNM707B 1. pNM706A (~11.6 kb)
2. pNM706B (~11.6 kb)

3. pNM707A (~9.6 kb)
4. pNM707B (~9.6 kb)

Figure 6:
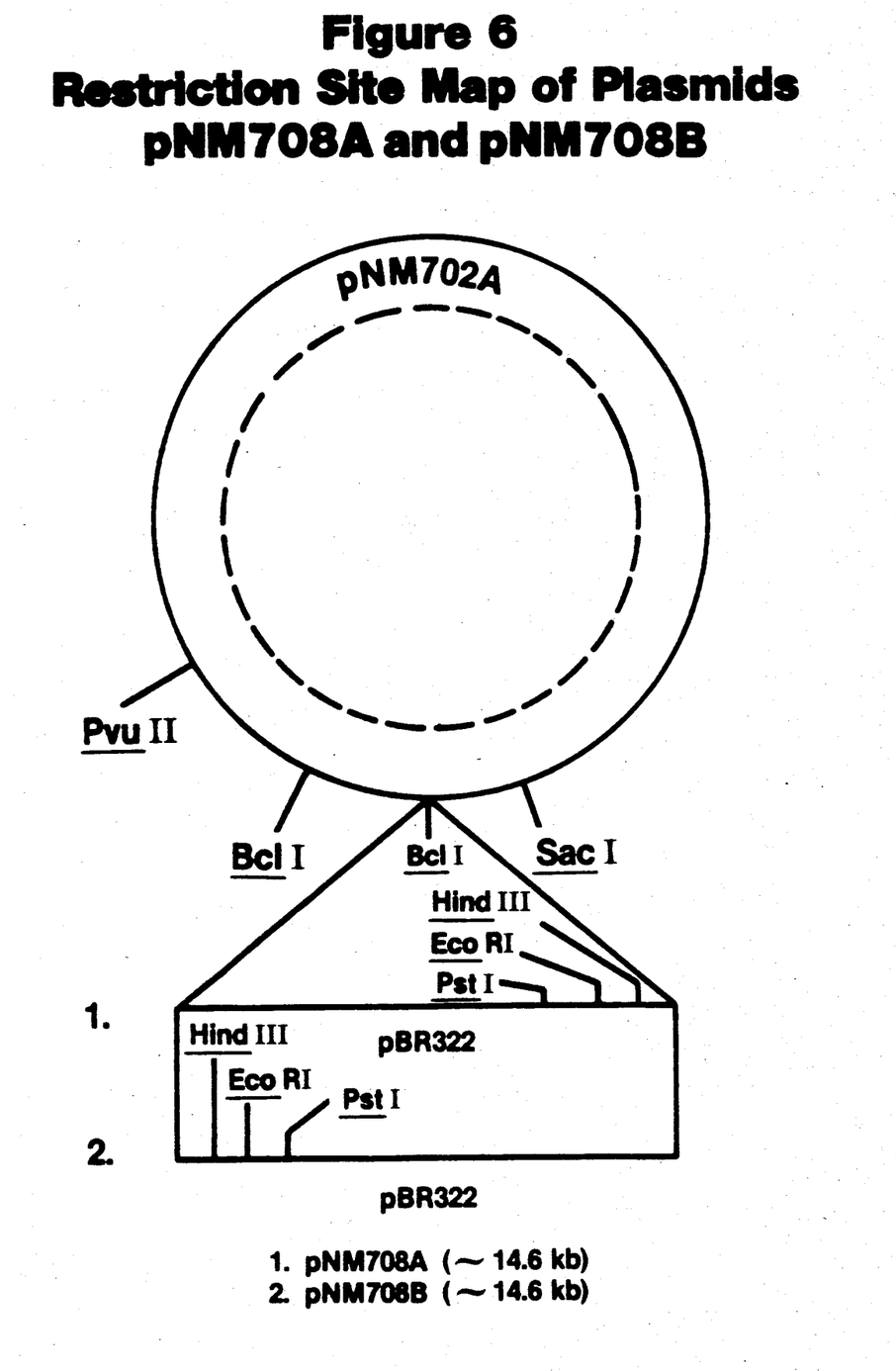

Figure 6
Restriction Site Map of Plasmids pNM708A and pNM708B 1. pNM708A (∼ 14.6 kb)
2. pNM708B (∼ 14.6 kb)

4,513,085

FUNCTIONALLY INDEPENDENT CLONING VECTORS FOR USE IN STREPTOMYCES

The present invention comprises novel recombinant DNA cloning vectors comprising a functionally independent origin of replication-containing restriction fragment of plasmid pEL7 and one or more DNA segments that confer resistance to antibiotics. The invention further comprises transformants of the aforementioned vectors.

The present invention is related generally to the pairs of recombinant DNA cloning vectors disclosed in U.S. patent application Ser. No. 312,446 filed on Oct. 19, 1981 now U.S. Pat. No. 4,416,994. The aforementioned pairs of vectors comprise plasmid pEL7 and a second plasmid which is functionally dependent on plasmid pEL7 and which comprises a restriction fragment of pEL7 and one or more DNA segments that confer resistance to antibiotics. The vectors of the present invention are readily distinguishable both structurally and also in that they are not functionally dependent and thus do not require the presence of plasmid pEL7 for replication and expression of antibiotic resistance.

The present invention provides antibiotic resistance-conferring cloning vectors for use in Streptomyces and related host cells. Heretofore, the development and exploitation of recombinant DNA technology in the above organisms has been retarded and made especially difficult because of the general lack of selectable genetic markers on cloning vectors. The vectors of the present invention are functionally independent and selectable in both Streptomyces and other host strains and therefore represent a significant advance in the technical art.

The present vectors are particularly useful because they are functionally independent, small, versatile and can be transformed and selected in any Streptomyces cell that is sensitive to an antibiotic for which resistance is conveyed. Since over half of the clinically important antibiotics are produced by Streptomyces strains, it is desirable to develop functionally independent cloning systems and vectors that are applicable to that industrially important group. The present invention provides such vectors and thus allows for the cloning of genes into Streptomyces both for increasing the yields of known antibiotics as well as for the production of new antibiotics and antibiotic derivatives.

The present invention provides vehicles for cloning DNA into Streptomyces host cells and also allows for the convenient selection of transformants. Since transformation is a very low frequency event, such a functional test is a practical necessity for determining which cell(s), of among the millions of cells, has acquired the plasmid DNA. This is important because DNA sequences that are non-selectable can be inserted onto the vectors and, upon transformation, cells containing the vector and the particular DNA sequence of interest can be isolated by appropriate antibiotic selection.

For purposes of the present invention as disclosed and claimed herein, the following terms are as defined below.

Recombinant DNA Cloning Vector—any autonomously replicating agent, including but not limited to plasmids, comprising a DNA molecule to which one or more additional DNA segments can or have been added.

Transformation—the introduction of DNA into a recipient host cell that changes the genotype and consequently results in a change in the recipient cell.

Transformant—a recipient host cell that has undergone transformation.

Functionally Dependent—the condition whereupon plasmid replication and expression of resistance to one or more antibiotics in a host cell requires the presence of a separate and different plasmid.

Functionally Independent—the condition whereupon plasmid replication and expression of resistance to one or more antibiotics in a host cell occurs in the absence of a separate and different plasmid.

Sensitive Host Cell—a host cell that cannot grow in the presence of a given antibiotic without a DNA segment that confers resistance thereto.

Restriction Fragment—any linear portion or whole of plasmid or chromosomal DNA generated by the action of one or more restriction enzymes.

Insertional Isomer—one of the two or more possible recombinant DNA molecules formed when a DNA fragment is inserted at one of two or more compatible sites on the recipient DNA.

Plasmid pLR2 ~1.6 kb BamHI Restriction Fragment—substantially the same ~1.6 kb BamHI thiostrepton resistance-conferring fragment contained in plasmid pIJ6.

Plasmid pLR1 or pLR4 ~3.4 kb BamHI Restriction Fragment—the same ~3.4 kb BamHI neomycin resistance-conferring fragment contained in plasmid pIJ2.

$Amp^R$—the ampicillin resistant phenotype.

$Tet^S$—the tetracycline sensitive phenotype.

$Thio^R$—the thiostrepton resistant phenotype.

$Neo^R$—the neomycin resistant phenotype.

DETAILED DESCRIPTION OF THE INVENTION

The present invention comprises functionally independent recombinant DNA cloning vectors comprising:

(a) a functional origin of replication-containing restriction fragment of plasmid pEL7 and
(b) one or more DNA segments that confer resistance to at least one antibiotic when transformed into a sensitive host cell, said host cell being susceptible to transformation, cell division, and culture.

The invention further comprises transformants of the aforementioned vectors.

The vectors of the present invention are constructed by ligating one or more antibiotic resistance-conferring DNA segments into an origin of replication-containing restriction fragment of plasmid pEL7. Plasmid pEL7, from which origin of replication-containing fragments are constructed, is ~10.9 kb and contains several restriction sites which are advantageous for molecular cloning. Since the origin of replication of plasmid pEL7 has been localized to within the ~6.78 kb BclI restriction fragment, a variety of different origin of replication-containing fragments can be generated by digesting the plasmid with restriction enzymes that cut outside the ~6.78 kb BclI region. A detailed restriction site map of plasmid pEL7 is presented in FIG. 1 of the accompanying drawings. For purposes of the present application, FIG. 1 and all subsequent figures are not drawn to scale.

Plasmid pEL7 can be conventionally isolated from *Streptomyces ambofaciens*/pEL7, a strain deposited and made part of the permanent stock culture collection of the Northern Regional Research Laboratory, Peoria, Ill., under the accession number NRRL 12523. It is available to the public as a preferred source and stock reservoir of the plasmid.

Although many different origin of replication-containing fragments of plasmid pEL7 can be constructed, the ~6.78 kb BclI restriction fragment is exemplified herein for illustrative purposes. This fragment can be independently ligated to one or more antibiotic resistance-conferring DNA segments, exemplified herein by the thiostrepton resistance-conferring ~1.6 kb BamHI or ~0.8 kb BclI restriction fragment of plasmid pLR2, the neomycin resistance-conferring ~3.4 kb BamHI restriction fragment of plasmid pLR1 or plasmid pLR4 and the ~2.8 kb SalI fragment of plasmid pIJ43, to form functionally independent vectors illustrative of the present invention.

Plasmid pLR2, the source of the thiostrepton resistance-conferring fragment, is ~18.7 kb and is constructed by ligating HindIII-treated plasmid pIJ6, disclosed in Thompson et al., 1980, Nature 286:525, to HindIII-treated plasmid pBR322. Plasmid pLR1, the source of the neomycin resistance-conferring fragment, is ~14.8 kb and is similarly constructed except that plasmid pIJ2, disclosed in Thompson et al., 1980, is substituted for plasmid pIJ6. An analogous construction, resulting in plasmid pLR4, is made by ligating BamHI-treated plasmid pBR322 to BamHI-treated plasmid pLR1. Plasmids pLR2, pLR1 and pLR4 are functional in E coli and therefore can be amplified and isolated conveniently for subsequent manipulation.

Plasmid pIJ43, the source of the erythromycin resistance-conferring fragment, can be obtained from E. coli 803/pIJ43, a strain deposited and made part of the permanent stock culture collection of the American Type culture Collection, Rockville, Md. It is available to the public as a preferred source and stock reservoir of the plasmid under the accession number ATCC 39156. A restriction site and functional map of each of plasmids pLR1, pLR2 and pLR4 is presented in FIG. 2 of the accompanying drawings.

For convenience and ease of construction, the thiostrepton resistance-conferring ~1.6 kb BamHI or ~0.8 kb BclI fragment, the neomycin resistance-conferring ~3.4 kb BamHI fragment and the erythromycin resistance-conferring ~2.8 kb SalI fragment are independently ligated to the ~6.78 kb origin of replication-containing BclI fragment of plasmid pEL7. The resulting recombinant DNA is then self ligated to produce functionally independent plasmids illustrative of the present invention. Recombinant plasmids of two orientations result depending upon the orientation of the particular resistance-conferring DNA fragment. Thus, ligation of the ~1.6 kb BamHI fragment of plasmid pLR2 into the ~6.78 kb BclI fragment of plasmid pEL7 results in illustrative plasmids pNM702A and pNM702B; ligation of the ~3.4 kb BamHI fragment of plasmid pLR1 or plasmid pLR4 results in illustrative plasmids pNM704A and pNM704B; and ligation of both of the fragments results in illustrative plasmids pNM705A and pNM705B. Similarly, ligation of the ~0.8 kb BclI fragment of plasmid pLR2 into the ~6.78 kb BclI fragment of plasmid pEL7 results in illustrative plasmids pNM703A and pNM703B; ligation of both the ~0.8 kb BclI and ~3.4 kb BamHI fragments results in illustrative plasmids pNM706A and pNM706B; and ligation of the ~2.8 kb SalI fragment provided with an appropriate linker, results in illustrative plasmids pNM707A and pNM707B.

Various plasmid pEL7 restriction fragments can be used for ligation of the antibiotic resistance-conferring DNA segments provided that the origin of replication contained in the ~6.78 kb BclI restriction fragment is present. Such plasmid pEL7 restriction fragments include, but are not limited to, the ~9.1 kb XhoI-SacI, ~10.9 kb SacI, ~4.75 kb XhoI-BclI and ~10.9 kb BclI fragments. In addition, a particular antibiotic resistance-conferring DNA segment is not limited to a single position but can be ligated or inserted into varying sites of plasmid pEL7 provided that the origin of replication or other critical plasmid controlled physiological functions are not disrupted. Those skilled in the art understand or can readily determine which sites are advantageous for the ligation or insertion of a particular DNA segment.

Although the thiostrepton, neomycin and erythromycin antibiotic resistance-conferring DNA segments are respectively exemplified by the ~1.6 kb BamHI or ~0.8 kb BclI fragment of plasmid pLR2, ~3.4 kb BamHI fragment of plasmid pLR1 and ~2.8 kb SalI restriction fragment of plasmid pIJ43, those skilled in the art can construct and use, either individually or in combination, additional DNA segments that also confer resistance to the aforementioned antibiotics. Additional thiostrepton resistance-conferring DNA segments of plasmid pLR2 include, for example, the ~13 kb PstI restriction fragment. Additional neomycin resistance-conferring DNA segments of plasmid pLR1 include, for example, the ~3.5 kb PstI restriction fragment and also the larger of the SacI-KpnI subfragments of the ~3.4 kb BamHI restriction fragment. Additional fragments that confer resistance to erythromycin include, for example, the ~2.5 kb SalI-BamHI, ~2.7 kb SalI-BglII, ~3.0 kb HindIII, ~2.8 kb XhoI-BglII, and the ~4.1 kb EcoRI-BamHI restriction fragments of plasmid pIJ43.

Still other DNA segments that confer resistance to the same or to different antibiotics such as, for example, chloramphenicol, streptomycin, hygromycin, viomycin, tylosin and the like can also be constructed and used by those skilled in the art. In addition, functional derivatives of these or any of the other antibiotic resistance-conferring DNA segments herein described can be constructed by adding, eliminating, or substituting certain nucleotides in accordance with the genetic code. Those skilled in the art will understand that ligation of these derivatives, or any other antibiotic resistance-conferring DNA segment, to plasmid pEL7 origin of replication-containing fragments results in functionally independent vectors that are also within the scope of the present invention.

The restriction fragments of plasmids pEL7 and also the various antibiotic resistance-conferring DNA segments can be modified to facilitate ligation. For example, molecular linkers can be provided to either or both of a particular plasmid pEL7 restriction fragment or a particular antibiotic resistance-conferring DNA segment. Thus, specific sites for subsequent ligation can be constructed conveniently. In addition, the origin of replication-containing restriction fragments can also be modified by adding, eliminating, or substituting certain nucleotides to provide a variety of restriction sites for ligation of DNA. Those skilled in the art understand nucleotide chemistry and the genetic code and thus which nucleotides are interchangeable and which DNA modifications are desirable for a specific purpose.

The present functionally independent vectors can also be ligated to a restriction fragment of an *E. coli* plasmid such as, for example, pBR322, pBR324, pBR325, pBR328 and the like, to produce functionally independent vectors that replicate and are selectable in both *E. coli* and Streptomyces. These bifunctional constructions comprise the pEL7 origin of replication, a DNA segment that confers antibiotic resistance in Streptomyces, a replicon that is functional in *E. coli* and also a DNA segment that confers antibiotic resistance in *E. coli*. Bifunctional constructions, exemplified herein by plasmids pNM708A and pNM708B, are particularly advantageous because amplification and manipulation of plasmids can be done faster and more conveniently in *E. coli* than in Streptomyces. Thus, after desired recombinant DNA procedures are accomplished within the *E. coli* host system, the entire plasmid or the particular Streptomyces DNA can be removed and re-constructed to plasmid form (if necessary), and then transformed into a Streptomyces or related host cell.

The functionally independent recombinant DNA cloning vectors of the present invention are not limited for use in a single species or strain of Streptomyces. To the contrary, the vectors are broadly applicable and can be transformed into host cells of many Streptomyces taxa, particularly restrictionless strains of economically important taxa that produce antibiotics such as aminoglycoside, macrolide, β-lactam, polyether and glycopeptide antibiotics. Such restrictionless strains are readily selected and isolated from Streptomyces taxa by conventional procedures well known in the art (Lomovskaya et al., 1980, Microbiological Reviews 44:206). Host cells of restrictionless strains lack restriction enzymes and therefore do not cut or degrade plasmid DNA upon transformation. For purposes of the present application, host cells containing restriction enzymes that do not cut any of the restriction sites of the present vectors are also considered restrictionless.

Preferred host cells of restrictionless strains of Streptomyces taxa that produce aminoglycoside antibiotics and in which the present functionally independent vectors are especially useful and can be transformed, include restrictionless cells of, for example: *S. kanamyceticus* (kanamycins), *S. chrestomyceticus* (aminosidine), *S. griseoflavus* (antibiotic MA 1267), *S. microsporeus* (antibiotic SF-767), *S. ribosidificus* (antibiotic SF733), *S. flavopersicus* (spectinomycin), *S. spectabilis* (actinospectacin), *S. rimosus* forma *paromomycinus* (paromomycins, catenulin), *S. fradiae* var. *italicus* (aminosidine), *S. bluensis* var. *bluensis* (bluensomycin), *S. catenulae* (catenulin), *S. olivoreticuli* var. *cellulophilus* (destomycin A), *S. tenebrarius* (tobramycin, apramycin), *S. lavendule* (neomycin), *S. albogriseolus* (neomycins), *S. albus* var. *metamycinus* (metamycin), *S. hygroscopicus* var. *sagamiensis* (spectinomycin), *S. bikiniensis* (streptomycin), *S. griseus* (streptomycin), *S. erythrochromogenes* var. *narutoensis* (streptomycin), *S. poolensis* (streptomycin), *S. galbus* (streptomycin), *S. rameus* (streptomycin), *S. olivaceus* (streptomycin), *S. mashuensis* (streptomycin), *S. hygroscopicus* var. *limoneus* (validamycins), *S. rimofaciens* (destomycins), *S. hygroscopicus* forma *glebosus* (glebomycin), *S. fradiae* (hybrimycins neomycins), *S. eurocidicus* (antibiotic A16316-C), *S. aquacanus* (N-methyl hygromycin B), *S. crystallinus* (hygromycin A), *S. noboritoensis* (hygromycin), *S. hygroscopicus* (hygromycins), *S. atrofaciens* (hygromycin), *S. kasugaspinus* (kasugamycins), *S. kasugaensis* (kasugamycins), *S. netropsis* (antibiotic LL-AM31), *S. lividus* (lividomycins), *S. hofuensis* (seldomycin complex), and *S. canus* (ribosyl paromamine).

Preferred host cells of restrictionless strains of Streptomyces taxa that produce macrolide antibiotics and in which the present functionally independent vectors are especially useful and can be transformed, include restrictionless cells of, for example: *S. caelestis* (antibiotic M188), *S. platensis* (platenomycin), *S. rochei* var. *volubilis* (antibiotic T2636), *S. venezuelae* (methymycins), *S. griseofuscus* (bundlin), *S. narbonensis* (josamycin, narbomycin), *S. fungicidicus* (antibiotic NA-181), *S. griseofaciens* (antibiotic PA133A, B), *S. roseocitreus* (albocycline), *S. bruneogriseus* (albocycline), *S. roseochromogenes* (albocycline), *S. cinerochromogenes* (cineromycin B), *S. albus* (albomycetin), *S. felleus* (argomycin, picromycin), *S. rochei* (lankacidin, borrelidin), *S. violaceoniger* (lankacidin), *S. griseus* (borrelidin), *S. maizeus* (ingramycin), *S. albus* var *coilmyceticus* (colermycin), *S. mycarofaciens* (acetyl-leukomycin, espinomycin), *S. hygroscopicus* (turimycin, relomycin, maridomycin, tylosin, carbomycin), *S. griseospiralis* (relomycin), *S. lavendulae* (aldgamycin), *S. rimosus* (neutramycin), *S. deltae* (deltamycins), *S. fungicidicus* var. *espinomyceticus* (espinomycins), *S. furdicidicus* (mydecamycin), *S. ambofaciens* (foromacidin D), *S. eurocidicus* (methymycin), *S. griseolus* (griseomycin), *S. flavochromogenes* (amaromycin, shincomycins), *S. fimbriatus* (amaromycin), *S. fasciculus* (amaromycin), *S. erythreus* (erythromycins), *S. antibioticus* (oleandomycin), *S. olivochromogenes* (oleandomycin), *S. spinichromogenes* var. *suragaoensis* (kujimycins), *S. kitasatoensis* (leucomycin), *S. narbonensis* var. *josamyceticus* (leucomycin A3, josamycin), *S. albogriseolus* (mikonomycin), *S. bikiniensis*, (chalcomycin), *S. cirratus* (cirramycin), *S. djakartensis* (niddamycin), *S. eurythermus* (angolamycin), *S. fradiae* (tylosin, lactenocin, macrocin), *S. goshikiensis* (bandamycin), *S. griseoflavus* (acumycin), *S. halstedii* (carbomycin), *S. tendae* (carbomycin), *S. macrosporeus* (carbomycin), *S. thermotolerans* (carbomycin) and *S. albireticuli* (carbomycin).

Preferred host cells of restrictionless strains of Streptomyces taxa that produce β-lactam antibiotics and in which the present functionally independent vectors are especially useful and can be transformed, include restrictionless cells of, for example: *S. lipmanii* (A16884, MM4550, MM13902), *S. clavuligerus* (A16886B, clavulanic acid), *S. lactamdurans* (cephamycin C), *S. griseus* (cephamycin A, B), *S. hygroscopicus* (deacetoxycephalosporin), *S. wadayamensis* (WS-3442-D), *S. chartreusis* (SF 1523), *S. heteromorphus* and *S. panayensis* (C2081X); *S. cinnamonensis*, *S. fimbriatus*, *S. halstedii*, *S. rochei* and *S. viridochromogenes* (cephamycins A, B); *S. cattleya* (thienamycin); and *S. olivaceus, S. flavovirens, S. flavus, S. fulvoviridis, S. argenteolus,* and *S. sioyaensis* (MM 4550 and MM 13902).

Preferred host cells of restrictionless strains of Streptomyces taxa that produce polyether antibiotics and in which the present functionally independent vectors are especially useful and can be transformed, include restrictionless cells of, for example: *S. albus* (A204, A286-95A and B, salinomycin), *S. hygroscopicus* (A218, emericid, DE3936), A120A, A28695A and B, etheromycin (dianemycin), *S. griseus* (grisorixin), *S. conglobatus* (ionomycin), *S. eurocidicus* var. *asterocidicus* (laidlomycin), *S. lasaliensis* (lasalocid), *S. ribosidificus* (lonomycin), *S. cacaoi* var. *asoensis* (lysocellin), *S. cinnamonensis* (monensin), *S. aureofaciens* (narasin), *S. gallinarius* (RP 30504), *S. longwoodensis* (lysocellin), *S. flaveolus*

(CP38936), *S. mutabilis* (S-11743a), and *S. violaceoniger* (nigericin).

Preferred host cells of restrictionless strains of Streptomyces taxa that produce glycopeptide antibiotics and in which the present functionally independent vectors are especially useful and can be transformed, include restrictionless cells of, for example: *S. orientalis* and *S. haranomachiensis* (vancomycin); *S. candidus* (A-35512, avoparcin), and *S. eburosporeus* (LL-AM 374).

Preferred host cells of other Streptomyces restrictionless strains in which the present functionally independent vectors are especially useful and can be transformed, include restrictionless cells of, for example: *S. lividans* 1326 (Bibb, M. J. et al., 1977, J. of Molecular and General Genetics 154:155, Schottel, J. L. et al., 1981, J. of Bacteriology 146 (1):360, and Bibb, M. J. et al., 1981, J. of Molecular and General Genetics 148:230), *S. coelicolor, S. granuloruber, S. roseosporus, S lividans, S. tenebrarius, S. espinosus, S. acrimycins, S. glaucescens, S. parvilin, S. pristinaespiralis, S. violaceoruber, S. vinaceus* and *S. azureus*.

In addition to the representative Streptomyces host cells described above, the present functionally independent vectors are also useful and can be transformed into cells of restrictionless strains of other taxa such as, for example: Bacillus, Staphylococcus and related Actinomycetes, including Streptosporangium, Actinoplanes, Nocardia, and Micromonospora. Thus, the vectors of the present invention have wide application and are useful and can be transformed into host cells of a variety of organisms.

While all the embodiments of the present invention are useful, some of the present recombinant DNA cloning vectors and transformants are preferred. Accordingly, preferred vectors are plasmids pNM702A, pNM703A, pNM704A, pNM705A, pNM706A, pNM707A and pNM708A; and preferred transformants are *Streptomyces ambofaciens*/pNM702A, *S. ambofaciens*/pNM703A, *S. lividans* 1326/pNM703A, *S. ambofaciens*/pNM704A, *S. ambofaciens*/pNM705A, *S. ambofaciens*/pNM706A, *S. ambofaciens*/pNM707A, *S. ambofaciens*/pNM708A and *E. coli* K12 HB101/pNM708A. Moreover, of this preferred group, plasmids pNM702A, pNM703A, pNM705A, and pNM707A and transformants *S. ambofaciens*/pNM702A, *S. ambofaciens*/pNM703A, *S. lividans* 1326/pNM703A, *S. ambofaciens*/pNM705A and *S. ambofaciens*/pNM707A are most preferred.

The functionally independent recombinant DNA cloning vectors and transformants of the present invention have broad utility and help fill the need for suitable cloning vehicles for use in Streptomyces and related organisms. Moreover, the ability of the present vectors to confer resistance to antibiotics that are toxic to non-transformed host cells, also provides a functional means for selecting transformants. This is important because of the practical necessity for determining and selecting the particular cells that have acquired vector DNA. Additional DNA segments, that lack functional tests for their presence, can also be inserted onto the present vectors and then transformants containing the non-selectable DNA can be isolated by appropriate antibiotic selection. Such non-selectable DNA segments can be inserted at any site, except within regions necessary for plasmid function and replication, and include, but are not limited to, genes that specify antibiotic modification enzymes and regulatory genes of all types.

More particularly, a non-selectable DNA segment that comprises a gene is inserted on a plasmid such as for example, illustrative plasmid pNM705A, at the central SalI or sub-terminal PvuII restriction site of the ~1.6 kb BamHI resistance-conferring fragment. Such an insertion inactivates the thiostrepton resistance gene and thus allows for the easy identification of transformants containing the recombinant plasmid. This is done by first selecting for neomycin resistance and, secondarily, identifying those neomycin resistant transformants that are not resistant to thiostrepton. In a similar manner, insertion of a DNA segment of interest at, for example, the internal BamHI restriction site of the ~3.4 kb BamHI resistance-conferring fragment inactivates the neomycin resistance gene. Thus, transformants carrying this recombinant plasmid also are identified easily by first selecting for thiostrepton resistance and, secondarily, identifying those thiostrepton resistant transformants that are not resistant to neomycin. Similar selection involving the insertional inactivation of the erythromycin gene can also be done. Therefore, the ability to select for antibiotic resistance in Streptomyces and related cells allows for the efficient isolation of the extremely rare cells that contain the particular non-selectable DNA of interest.

The functional test for antibiotic resistance, as described herein above, is also used to locate DNA segments that act as control elements and direct expression of an individual antibiotic resistance gene. Such segments, including but not limited to, promoters, attenuators, repressors, inducers, ribosomal binding sites, and the like, are used to control the expression of other genes in cells of Streptomyces and related organisms.

The thiostrepton, neomycin and erythromycin resistance-conferring functionally independent vectors of the present invention are also useful for insuring that linked DNA segments are stably maintained in host cells over many generations. These genes or DNA fragments, covalently linked to the thiostrepton, erythromycin or neomycin resistance-conferring fragment and propagated either in Streptomyces or in the cells of related organisms, are maintained by exposing the transformants to levels of thiostrepton, erythromycin or neomycin that are toxic to non-transformed cells. Therefore, transformants that lose the vector, and consequently any covalently linked DNA, cannot grow and are eliminated from the culture. Thus, the vectors of the present invention can stabilize and maintain any DNA sequence of interest.

The functionally independent cloning vectors and transformants of the present invention provide for the cloning of genes to improve yields of various products that are currently produced in Streptomyces and related cells. Examples of such products include, but are not limited to, Streptomycin, Tylosin, Cephalosporins, Actaplanin, Narasin, Monensin, Apramycin, Tobramycin, Erythromycin, and the like. The present invention also provides selectable vectors that are useful for cloning, characterizing and reconstructing DNA sequences that code for commercially important proteins such as, for example, human insulin, human proinsulin, glucagon, interferon, human growth hormone, bovine growth hormone and the like; for enzymatic functions in metabolic pathways leading to commercially important processes and compounds; or for control elements that improve gene expression. These desired DNA sequences include, but are not limited to, DNA that codes for enzymes that catalyze synthesis of derivatized antibiotics such as, for example, Streptomycin, Cephalosporin, Tylosin, Actaplanin, Narasin, Monensin, Apramycin, Tobramycin and Erythromycin derivatives, or for enzymes that mediate and increase bioproduction of antibiotics or other products. The capability for inserting and stabilizing such DNA segments thus allows for increasing the yield and availability of antibiotics that are produced by Streptomyces and related organisms.

*Streptomyces ambofaciens*/pEL7, as a source of plasmid pEL7, can be cultured in a number of ways using any of several different media. Carbohydrate sources which are preferred in a culture medium include, for example, molasses, glucose, dextrin, and glycerol, and nitrogen sources include, for example, soy flour, amino acid mixtures, and peptones. Nutrient inorganic salts are also incorporated and include the customary salts capable of yielding sodium, potassium, ammonia, calcium, phosphate, chloride, sulfate, and like ions. As is necessary for the growth and development of other microorganisms, essential trace elements are also added. Such trace elements are commonly supplied as impurities incidental to the addition of other constituents of the medium.

*Streptomyces ambofaciens*/pEL7 is grown under aerobic culture conditions over a relatively wide pH range of about 5 to 9 at temperatures ranging from about 15° to 40° C. For production of plasmid pEL7 at the highest copy number, however, it is desirable to start with a culture medium at a pH of about 6.5 and maintain a culture temperature of about 30° C. Culturing *Streptomyces ambofaciens*/pEL7, under the aforementioned conditions, results in a reservoir of cells from which plasmid pEL7 is isolated conveniently.

The following examples further illustrate and detail the invention disclosed herein. Both an explanation of and the actual procedures for constructing the invention are described where appropriate.

EXAMPLE 1

Isolation of Plasmid pEL7

A. Culture of *Streptomyces ambofaciens*/pEL7

A vegetative inoculum of *Streptomyces ambofaciens*/pEL7 (NRRL 12523) was conventionally prepared by growing the strain under submerged aerobic conditions in 50 ml. of sterilized vegetative medium with the following preferred composition.

| Ingredient | Amount |
| --- | --- |
| Glucose | 20 g./l. |
| Nutrisoy flour* | 15 g./l. |
| Corn steep liquor* | 10 g./l. |
| CaCO₃ | 2 g./l. |
| Water (tap) | 1.1 l. |

*Nutrisoy flour is obtained from Archer Daniels Midland Company, 4666 Faries Parkway, Decatur, Illinois 62526.
*Corn steep liquor is obtained from CPC International, Corn Products, P.O. Box 3000, Englewood, N.J. 07632.

The vegetative inoculum was incubated for 48 hours at a temperature of 30° C. and a pH of 6.5. After incubation, about 1.0 ml. of the inoculum was transferred to 50 ml. of sterilized cell production medium with the following preferred composition.

| Ingredient | Amount |
| --- | --- |
| Trypticase soy broth* | 30 g./l. |
| Glucose | 10 g./l. |

-continued

| Ingredient | Amount |
| --- | --- |
| Glycine | 1 g./l. |
| Deionized water | 1 g./l. |

*Trypticase soy broth is obtained from Difco Laboratories, Detroit, Michigan.

The inoculated cell production medium was incubated for about 20 hours at 30° C. The pH was not adjusted. After incubation, the *Streptomyces ambofaciens*/pEL7 cells were ready for harvest and subsequent isolation of plasmid DNA.

B. Plasmid Isolation

About 10 g. (wet wgt) of *Streptomyces ambofaciens*/pEL7 cells were harvested by centrifugation (10 minutes, 5° C., 10,000 rpm). The cells were homogenized using a tissue grinder, washed in TES buffer (0.05M tris(hydroxymethyl)aminomethane [tris], 0.005M EDTA, and 0.05M NaCl, pH 8.0), and then suspended in TES buffer containing 25% sucrose. After the addition of about 120 mg. of lysozyme in 20 ml. of TES-25% sucrose buffer, the suspension was incubated at 35°–37° C. for about 20 minutes and, upon addition of 40 ml. of 0.25M EDTA, pH 8.0, the suspension was again incubated at 35° C. for 10 minutes. Following this, about 40 ml. of 5% SDS (sodium dodecyl sulfate) in TE buffer (0.01M tris, 0.001M EDTA, pH 8.0) was added and then, after the resultant mixture was again incubated at 35°–37° C. for 20 minutes, about 50 ml. of 5M NaCl in deionized water was added. The mixture was stirred, placed on an ice bath for about 4 hours and then centrifuged (30 minutes, 4° C., 10,000 rpm). About 0.313 volumes of 42% polyethylene glycol in deionized water were added to the NaCl supernatant and the resulting mixture was cooled at 4° C. for about 18 hours. The DNA precipitate was collected by centrifugation (5 minutes, 4° C., 3000 rpm) and was then dissolved in TES buffer at pH 8.0. Centrifugation (40 hours, 15° C., 35,000 rpm) using cesium chloride and ethidium bromide gradients separated the DNA into two well defined bands with the lower band constituting the desired plasmid pEL7. Following conventional procedures, the plasmid band was removed, washed twice with isoamyl alcohol, dialyzed over TE buffer at pH 8.0 and precipitated with ethanol. The thus isolated plasmid pEL7 DNA was dissolved in 0.4 ml. of TE buffer at pH 8.0, and was then frozen at −20° C. for storage.

EXAMPLE 2

Construction of Plasmid pLR2

A. HindIII Digestion of Plasmid pIJ6

About 20 μl. (20 μg.) of plasmid pIJ6 DNA, disclosed in Thompson et al., 1980, Nature 286:525, 5 μl. BSA (Bovine serum albumin, 1 mg./ml), 19 μl. water, 1 μl. of HindIII (containing 3 new England Bio Lab Units) restriction enzyme* and 5 μl. reaction mix** were incubated at 37° C. for 2 hours. The reaction was terminated by the addition of about 50 μl. of 4M ammonium acetate and 200 μl. of 95% ethanol. The resultant DNA precipitate was washed twice in 70% ethanol, dried in vacuo, suspended in 20 μl. of TE buffer, and frozen at −20° C. for storage.

*Restriction enzymes can be obtained from the following sources:

New England Bio Labs., Inc.
32 Tozer Rd.
Beverly, Mass. 01915

Boehringer-Mannheim Biochemicals
7941 Castleway Dr.
Indianapolis, Ind. 46250

**Reaction mix for HindIII restriction enzyme was prepared with the following composition.

L 600 mM NaCl
100 mM Tris-HCl, pH 7.9
70 mM MgCl$_2$
10 mM Dith-othreitol

B. HindIII Digestion of Plasmid pBR322

About 8 μl. (4 μg.) of plasmid pBR322 DNA, 5 μl. reaction mix, 5 μl. BSA (1 mg./ml.), 31 μl. water and 1 μl. of HindIII restriction enzyme were incubated at 37° C. for 2 hours. After the reaction was terminated by incubating at 60° C. for 10 minutes, about 50 μl. of ammonium acetate and 200 μl. of 95% ethanol were added. The resultant DNA precipitate was washed twice in 70% ethanol, dried in vacuo, and suspended in 45 μl. of water.

C. Ligation of HindIII Digested Plasmids pIJ6 and pBR322

About 20 μl. of HindIII treated plasmid pIJ6 (from Example 2A), 20 μl. of HindIII treated plasmid pBR322 (from Example 2B), 5 μl. BSA (1 mg./ml.), 1 μl. of T4 DNA ligase*, and 5 μl. ligation mix** were incubated at 16° C. for 4 hours. The reaction was terminated by the addition of about 50 μl. 1.4M ammonium acetate and 200 μl. of 95% ethanol. The resultant DNA precipitate was washed twice in 70% ethanol, dried in vacuo, and suspended in TE buffer. The suspended DNA constituted the desired plasmid pLR2.
*T4 DNA ligase can be obtained from the following source:

New England Bio Labs., Inc.
32 Tozer Rd.
Beverly, Mass. 01915

**Ligation mix was prepared with the following composition:

500 mM Tris—HCl, pH 7.8
200 mM Dithiothreitol
100 mM MgCl$_2$
10 mM ATP

EXAMPLE 3

Construction of E. coli K12 HB101/pLR2

About 10 ml. of frozen competent E. coli K12 HB101 cells (Bolivar et al., 1977, Gene 2:75-93) were pelleted by centrifugation and then suspended in about 10 ml. of 0.01M sodium chloride. Next, the cells were pelleted again, resuspended in about 10 ml. of 0.03M calcium chloride solution, incubated on ice for 20 minutes, pelleted a third time and finally resuspended in 1.25 ml. of 0.03M calcium chloride solution. The resultant cell suspension was competent for subsequent transformation.

Plasmid pLR2 in TE buffer (prepared in Example 2C) was ethanol precipitated, suspended in 150 ||l. of 30 mM calcium chloride solution and gently mixed in a test tube with about 200 ||l. of competent E. coli K12 HB101 cells. The resultant mixture was incubated on ice for about 45 minutes and then at 42° C. for about 1 minute. Next, about 3 ml. of L-broth (Bertani, 1951, J. Bacteriology 62:293) containing 50 μg./ml. of ampicillin was added. The mixture was incubated with shaking at 37° C. for 1 hour and then plated on L-agar (Miller, 1972, Experiments in Molecular Genetics, Cold Spring Harbor Labs, Cold Spring Harbor, N.Y.) containing ampicillin. Surviving colonies were selected and tested for the expected phenotype (Amp$^R$, Tet$^S$,) and constituted the desired E. coli K12 HB101/pLR2 transformants.

EXAMPLE 4

Construction of Plasmid pLR1

Plasmid pLR1 was prepared in substantial accordance with the teaching of Example 2A-C except that plasmid pIJ2, disclosed in Thompson et al., 1980, Nature 286:525, was used in place of plasmid pIJ6. The desired plasmid pLR1 was suspended in TE buffer.

EXAMPLE 5

Construction of E. coli K12 HB101/pLR1

The desired construction was carried out in substantial accordance with the teaching of Example 3 except that plasmid pLR1, rather than plasmid pLR2, was used for transformation. Surviving colonies were selected and tested for the expected phenotype (Amp$^R$, Tet$^S$,) and constituted the desired E. coli K12 HB101/pLR1 transformants.

EXAMPLE 6

Construction of Plasmid pLR4

A. Partial BamHI Digestion of Plasmid pLR1

About 10 μl. (10 μg.) of plasmid pLR1, 5 μl. BSA (1 mg./ml.), 29 μl. water, 1 μl. of BamHI (diluted 1:4 with water) restriction enzyme, and 5 μl. reaction mix* were incubated at 37° C. for 15 minutes. The reaction was terminated by the addition of about 50 μl. of 4M ammonium acetate and 200 μl. of 95% ethanol. The resultant DNA precipitate was washed twice in 70% ethanol, dried in vacuo, and suspended in 20 μl. water.
*Reaction mix for BamHI restriction enzyme was prepared with the following composition.

1.5M NaCl
60 mM Tris—HCl, pH7.9
60 mM MgCl$_2$

B. BamHI Digestion of Plasmid pBR322

The desired digestion was carried out in substantial accordance with the teaching of Example 2B except that BamHI restriction enzyme was used in place of HindIII restriction enzyme. The digested plasmid pBR322 was suspended in 29 μl. of water.

C. Ligation of Partial BamHI Digested Plasmid pLR1 and BamHI Digested Plasmid pBR322

The desired ligation was carried out in substantial accordance with the teaching of Example 2C. The resultant ligated DNA was suspended in TE buffer and constituted the desired plasmid pLR4.

EXAMPLE 7

Construction of E. coli K12 HB101/pLR4

The desired construction was carried out in substantial accordance with the teaching of Example 3 except that plasmid pLR4, rather than plasmid pLR2, was used for transformation. Suriving colonies were selected and tested for the expected phenotype (Amp$^R$, Tet$^S$) and constituted the desired E. coli K12 HB101pLR4 transformants.

EXAMPLE 8

Construction of Plasmids pNM702A and pNM702B

A. BamHI Digestion of Plasmid pLR2 and Isolation of the ~1.6 kb Thiostrepton Resistance-Conferring Fragment About 25 μg. of plasmid pLR2 DNA, 10 μl. reaction mix, 5 μl. 0.1 M dithiothreitol, 10 μl. BSA (1 mg./ml.), 45 μl. water, and 5 μl. (4 units/μl.) of BamHI restriction enzyme were incubated at 37° C. for 2 hours. After adding an equal volume of 4M ammonium acetate and 2 volumes of 95% ethanol, the mixture was cooled at −20° C. for about 18 hours to precipitate the DNA. The DNA precipitate was collected by centrifugation and then suspended in about 50 μl. of TE buffer. The desired ~1.6 kb BamHI restriction fragment was isolated conventionally from the DNA suspension by agarose gel electrophoresis in substantial accordance with the teaching of Wieslander, L., 1979, Analytical Biochemistry 98:305. Following isolation, the fragment was resuspended in about 20 μl. of TE buffer for subsequent ligation.

B. BclI Digestion of Plasmid pEL7

The desired digestion was carried out at ~50° C. in substantial accordance with the teaching of Example 8A except that plasmid pEL7 and BclI restriction enzyme and reaction mix*, rather than plasmid pLR2 and BamHI restriction enzyme and reaction mix, were used. In addition, the DNA digest was not electrophoresed but was suspended directly in 20 μl. of TE buffer for subsequent ligation.

*Reaction mix for BclI reaction mix was prepared with the following composition.

12 mM NaCl
12 mM Tris—HCl, pH7.4
12 mM MgCl$_{12}$
0.5 mM Dithiothreitol

C. Ligation

A mixture of about 20 μg. of BclI restricted plasmid pEL7 DNA, 10 μg. of the ~1.6 kb BamHI restriction fragment of plasmid pLR2, 5 μl. BSA (1 mg./ml.), 10 μl. ligation mix, 45 μl. water and 3.5 μl. T4 DNA ligase were incubated at about 16° C. for about 18 hours. After adding 0.1 volume of 3M ammonium acetate and 2 volumes of cold ethanol, the mixture was cooled to −20° C. for about 18 hours to precipitate the DNA. The DNA precipitate was collected by centrifugation, washed with 70% ethanol, collected again and then suspended in 50 μl. of medium P (Hopwood and Wright, 1978, J. Molecular and General Genetics 162:307) for subsequent transformation.

Recombinant plasmids of two orientations result depending upon the orientation of the inserted ~1.6 kb BamHI thiostrepton resistance-conferring fragment. plasmid pNM702A designates the resultant recombinant plasmid in which the sub-terminal SalI restriction site of the resistance-conferring fragment is inserted closest to the flanking SacI site of plasmid pEL7. Plasmid pNM702B designates the recombinant plasmid with the reverse orientation. Thus, the final DNA suspension contains plasmids pNM702A and pNM702B. A restriction site map of each of plasmids pNM702A and pNM702B is presented in FIG. 3 of the accompanying drawings.

EXAMPLE 9

Construction of Streptomyces ambofaciens/pEL702A and S. ambofaciens/pEL702B

Using about 2 μg. DNA from Example 8C and 1×10$^8$ protoplasts of Streptomyces ambofaciens, a strain deposited and made part of the stock culture collection of the Northern Regional Research Laboratory, Peoria, Ill., from which it is available to the public under the accession number NRRL 2420, the desired constructions were made in substantial accordance with the teaching of International Publication (of International Patent Application No. PCT/GB 79/00095) No. WO79/01169, Example 2. The desired transformants were selected for thiostrepton resistance by plating on Bennett's Modified Medium* containing about 50 μg./ml. of antibiotic thiostrepton. The resultant Streptomyces ambofaciens/pNM702A and S. ambofaciens/pNM702B thiostrepton resistant colonies were isolated, cultured, and then conventionally identified by restriction enzyme and agarose gel electrophoretic analysis of the constitutive plasmids (Wieslander, 1979). The transformant cultures were used for subsequent production and isolation of their respective plasmids.

*Bennett's medium (Agar), disclosed in Waksman, 1961, The Actinomycetes, Vol. II, The Williams and Wilkins Company, Baltimore, Md., was modified by adding CoCl$_2$.6H$_2$O (0.01 g./L.) and by replacing glucose with dextrin.

EXAMPLE 10

Construction of Plasmids pNM704A and pNM704B

A. BamHI Digestion of Plasmid pLR1 and Isolation of the ~3.4 kb Neomycin Resistance-Conferring Fragment About 50 μg. of plasmid pLR1 DNA, 20 μl. reaction mix*, 10 μl. 0.1 M dithiothreitol, 20 μl. BSA (1 mg./ml.), 45 ml. water and 5 μl. (4 units/μl.) of BamHI restriction enzyme* were incubated at 37° C. for 2 hours. After adding an equal volume of 4 M ammonium acetate and 2 volumes of 95% ethanol, the mixture was cooled at −20° C. for about 18 hours to precipitate the DNA. The DNA precipitate was collected by centrifugation and then suspended in about 50 μl. of TE buffer. The desired ~3.4 kb BamHI restriction fragment was isolated conventionally from the DNA suspension by agarose gel electrophoresis (Wieslander, 1979). Following isolation, the fragment was resuspended in about 20 μl. of TE buffer for subsequent ligation.

B. Ligation

The desired ligation is carried out by reacting about 20 μg. of BclI restricted plasmid pEL7 DNA (prepared in Example 8B) and about 19 μg. of the ~3.4 kb BamHI restriction fragment of plasmid pLR1 in substantial accordance with the teaching of Example 8C.

Recombinant plasmids of two orientations result depending upon the orientation of the inserted ~3.4 kb BamHI neomycin resistance-conferring fragment. Plasmid pNM704A designates the recombinant plasmid in which the sub-terminal PstI restriction site of the resistance-conferring fragment is inserted closest to the flanking SacI site of plasmid pEL7. Plasmid pNM704B designates the recombinant plasmid with the reverse orientation. Thus, the final DNA suspension contains plasmids pNM704A and pNM704B. A restriction site map of each of plasmids pNM704A and pNM704B is presented in FIG. 3 of the accompanying drawings.

EXAMPLE 11

Construction of *Streptomyces ambofaciens*/pNM704A and *S. ambofaciens*/pNM704B

Using about 2 μg. DNA from Example 10C and 1×10⁸ protoplasts of *Streptomyces ambofaciens*, (NRRL No. 2420), the desired constructions are made in substantial accordance with the teaching of International Publication (of International Patent Application No. PCT/GB 79/00095) No. WO79/01169, Example 2. The desired transformants are selected for neomycin resistance by plating on Bennett's Modified Medium containing about 1 μg./ml. of antibiotic neomycin*. The resultant *Streptomyces ambofaciens*/pNM704A and *S. ambofaciens*/pNM704B neomycin resistant colonies are isolated, cultured and then conventionally identified by restriction enzyme and agarose gel electrophoretic analysis of the constitutive plasmids (Weislander, 1979). The transformant cultures are used for subsequent production and isolation of their respective plasmids.

*Antibiotic neomycin can be obtained from Sigma, St. Louis, Mo.

EXAMPLE 12

Construction of Plasmids pNM705A and pNM705B

A. Isolation of Plasmids pNM702A

The desired plasmid is isolated from *Streptomyces ambofaciens*/pNM702A (prepared in Example 9 and cultured according to the teaching of Example 1A) in substantial accordance with the isolation procedure of Example 1B. The thus isolated plasmid pNM702A DNA is suspended in TE buffer at pH 8.0 for subsequent restriction enzyme digestion.

B. Partial BclI Digestion of Plasmid pNM702A

The desired digestion is carried out in substantial accordance with the teaching of Example 6A except that plasmid pNM702A DNA and BclI restriction enzyme and reaction mix, rather than plasmid pLR4 and BamHI restriction enzyme and reaction mix, are used. The thus digested DNA is suspended in 20 μl. of TE buffer for subsequent ligation with the ~3.4 kb BamHI restriction fragment of plasmid pLR1.

C. Ligation

The desired ligation is carried out by reacting about 20 μg. of the BclI restricted plasmid pNM702A DNA and about 10 μg. of the ~3.4 kb BamHI restriction fragment (prepared in Example 10A) in substantial accordance with the teaching of Example 10C.

Recombinant plasmids of two orientations result depending upon the orientation of the inserted ~3.4 kb BamHI neomycin resistance-conferring fragment. Plasmid pNM705A designates the recombinant plasmid in which the sub-terminal PstI site of the resistance-conferring fragment is inserted closest to the flanking SacI site of plasmid pNM702A. Plasmid pNM705B designates the recombinant plasmid with the reverse orientation. In addition, the insertional isomers of plasmids pNM705A and pNM705B are also produced since plasmid pNM702A has two BclI restriction sites for the insertion of the neomycin resistance-conferring fragment. A restriction site map of each of plasmids pNM705A and pNM705B is presented in FIG. 4 of the accompanying drawings.

EXAMPLE 13

Construction of *Streptomyces ambofaciens*/pNM705A and *S. ambofaciens*/pNM705B

Using about 2 μg. DNA from Example 12C and 1×10⁸ protoplasts of *Streptomyces ambofaciens*, (NRRL No. 2420), the desired constructions are made in substantial accordance with the teaching of International Publication (of International Patent Application No. PCT/GB 79/00095) No. WO79/01169, Example 2. The desired transformants are selected for thiostrepton and neomycin resistance by plating on Bennett's Modified Medium containing about 50 μg./ml. of antibiotic thiostrepton and 1 μg./ml. of antibiotic neomycin. The resultant *Streptomyces ambofaciens*/pNM705A and *S. ambofaciens*/pNM705B thiostrepton and neomycin resistant colonies are conventionally isolated, cultured and then identified by restriction enzyme and agarose gel electrophoretic analysis of the constitutive plasmids (Wieslander, 1979). The transformant cultures are used for subsequent production and isolation of their respective plasmids.

EXAMPLE 14

Construction of Plasmids pNM703A and pNM703B

A. BclI Digestion of Plasmid pLR2 and Isolation of the ~0.8 kb Thiostrepton Resistance-Conferring Fragment The desired digestion was carried out in substantial accordance with the teaching of Example 8A except that BclI restriction enzyme and reaction mix, rather than BamHI restriction enzyme and reaction mix, were used. The desired ~0.8 kb BclI restriction fragment was isolated conventionally from the DNA suspension by agarose gel electrophoresis in substantial accordance with the teaching of Weislander, 1979. Following isolation, the fragment was resuspended in about 20 μl. of TE buffer for subsequent ligation.

B. Ligation

About 20 μg. of BclI restricted plasmid pEL7 DNA (prepared in Example 8B) and 10 μg. of the ~0.8 kb BclI restriction fragment of plasmid pLR2 were ligated in substantial accordance with the teaching of Example 8C.

Recombinant plasmids of two orientations result depending upon the orientation of the inserted ~0.8 kb BclI thiostrepton resistance-conferring fragment. Plasmid pNM703A designates the resultant recombinant plasmid in which the sub-terminal PvuII restriction site of the resistance-conferring fragment is inserted away from (not closest to) the flanking SacI site of plasmid pEL7. Plasmid pNM703B designates the recombinant plasmid with the reverse orientation. Thus, the final DNA suspension contains plasmids pNM703A and pNM703B. A restriction site map of each of plasmids pNM703A and pNM703B is presented in FIG. 4 of the accompanying drawings.

EXAMPLE 15

Construction of *Streptomyces ambofaciens*/pNM703A and *S. ambofaciens*/pNM703B

Using DNA prepared in Example 14, the desired transformants were constructed in substantial accordance with the teaching of Example 9. The resultant *Streptomyces ambofaciens*/pNM703A and *S. ambofaciens*/pNM703B thiostrepton resistant colonies were isolated, cultured and then conventionally identified by restriction enzyme and agarose gel electrophoretic analysis of the constitutive plasmids (Weislander, 1979). The transformant cultures were used for subsequent production and isolation of their respective plasmids.

EXAMPLE 16

Construction of Plasmids pNM706A and pNM706B

The desired constructions are made in substantial accordance with the teaching of Example 12A-C except that plasmid pNM703A (isolated from Streptomyces ambofaciens/pNM703A of Example 15), rather than plasmid pNM704A, is used.

Recombinant plasmids of two orientations result depending upon the orientation of the inserted ~3.4 kb BamHI neomycin resistance-conferring fragment. Plasmid pNM706A designates the recombinant plasmid in which the sub-terminal PstI restriction site of the resistance-conferring fragment is inserted closest to the flanking SacI site of plasmid pNM703A. Plasmid pNM706B designates the recombinant plasmid with the reverse orientation. In addition, the insertional isomers of plasmids pNM706A and pNM706B are also produced since plasmid pNB703A has two BclI restriction sites for the insertion of the neomycin resistance-conferring fragment. A restriction site map of each of plasmids pNM706A and pNM706B is presented in FIG. 5 of the accompanying drawings.

EXAMPLE 17

Construction of Steptomyces ambofaciens/pNM706 and S. ambofaciens/pNM706B

Using about 2 μg. of DNA from Example 16, the desired constructions are made in substantial accordance with the teaching of Example 13. The resultant Streptomyces ambofaciens/pNM706 A and S. ambofaciens/pNM 706B thiostrepton and neomycin resistant colonies are conventionally isolated, cultured and then identified by restriction enzyme and agarose gel electrophoretic analysis of the constitutive plasmids (Weislander, 1979). The transformant cultures are used for subsequent production and isolation of their respective plasmids.

EXAMPLE 18

Construction of Plasmids pNM707A and pNM707B

A. Culture of E. coli 803/pIJ43 and Isolation of Plasmid pIJ43

The desired culturing of E. coli 803/pIJ43 (ATCC 39156) and the subsequent isolation of plasmid pIJ43 are both carried out in substantial accordance with the teaching of Davis, R. W. et al., 1980, A Manual For Genetic Engineering, Advanced Bacterial Genetics, Cold Spring Harbor Laboratories, Cold Spring Harbor, N.Y. The pIJ43 DNA is conventionally suspended in TE buffer and then cooled to −20° C. for storage.

B. Digestion and Isolation of ~2.8 kb SalI Fragment of plasmid pIJ43

About 20 μg. of plasmid pIJ43 DNA, 10 μl. reaction mix*, 10 μl. BSA (1 mg./ml.) 39 μl. water, and 1 μl. of SalI restriction enzyme (prepared by diluting in such a manner that 1 μl. contains about 60 New England Bio. Lab. units) were incubated at ambient temperature for about 60 minutes. After adding an equal volume of 4M ammonium acetate and 2 volumes of 95% ethanol, the mixture was cooled at −20° C. for about 18 hours to precipitate the DNA. The DNA precipitate was collected by centrifugation. The desired ~2.8 kb SalI fragments are separated and isolated conventionally by agarose gel electrophoresis (Weislander, 1979).

*Reaction mix for SalI restriction enzyme was prepared with the following composition.

1.5 M NaCl
60 mM Tris—HCl, pH 7.9
60 mM MgCl$_2$
60 mM 2-mercaptoethanol

C. Addition of BclI Linkers to the ~2.8 kb SalI Fragment of Plasmid pIJ43

The addition of BclI linkers* is carried out in substantial accordance with the teaching of Ullrich et al., 1977, Science 196:1313. The resultant fragment is treated with BclI restriction enzyme to produce the desired BclI sticky termini. The ~2.8 kb BclI fragment is then isolated according to known procedures and stored for subsequent ligation.

*BclI[d(CGGATCCG)] and other linkers are readily available at:

Collaborative Research Inc.
128 Spring Street
Lexington, Mass. 02173

D. Ligation

About 1 μg. of BclI digested plasmid pEL7 (prepared in Example 8B) and 1 82 g. of the ~2.8 kb fragment of plasmid pIJ43 (prepared in Example 18B and C), are ligated in substantial accordance with the teaching of Example 8C.

Recombinant plasmids of two orientations result depending upon the orientation of the inserted ~2.8 kb BclI erythromycin resistance-conferring fragment. Plasmid pNM707A designates the recombinant plasmid in which the sub-terminal PstI site of the resistance-conferring fragment is inserted closest to the flanking SacI site of plasmid pEL7. Plasmid pNM707B designates the recombinant plasmid with the reverse orientation. A site map of each of plasmids pNM707A and pNM707B is presented in FIG. 5 of the accompanying drawings.

EXAMPLE 19

Construction of Streptomyces ambofaciens/pNM707A and S. ambofaciens/pNM707B

The desired constructions are made in substantial accordance with the teaching of Example 9 except that plasmid pNM707A and pNM707B DNA, rather than DNA from Example 8C, is used. The desired transformants are selected for erythromycin resistance by overlaying the regenerating protoplasts with R2 medium top agar containing sufficient erythromycin to bring the plate concentration to 50 μg./ml. The resultant Streptomyces ambofaciens/pNM707A and S. ambofaciens/pNM707B erythromycin resistant colonies are isolated according to known procedures, cultured and then conventionally identified by restriction enzyme and agarose gel electrophoretic analysis of the constitutive plasmids (Wieslander, 1979). The transformant cultures are used for subsequent production and isolation of their respective plasmids.

EXAMPLE 20

Construction of Plasmids pNM708A and pNM708B

A. Addition of BclI Linkers to BamHI Digested Plasmid pBR322

The addition of BclI linkers to BamHI digested plasmid pBR322 (prepared in Example 6B) is carried out in substantial accordance with the teaching of Ullrich et al., 1977, Science 196:1313. The resultant fragment is treated with BclI restriction enzyme to produce the desired BclI sticky termini. The fragment is then isolated according to known procedures and stored for subsequent ligation.

B. Ligation

About 20 µg. of the partial BclI digest of plasmid pNM702A (prepared in Example 12B) and about 10 µg. of the plasmid pBR322 DNA with BclI sticky termini are ligated in substantial accordance with the teaching of Example 2C. The resultant DNA is washed twice in 70% ethanol, dried in vacuo and suspended in TE buffer.

Recombinant plasmids of two orientations result depending upon the orientation of the inserted pBR322 fragment. Plasmid pNM708A designates the recombinant plasmid in which the sub-terminal HindIII restriction site of the pBR322 fragment is inserted closest to flanking SacI site of plasmid pNM702A. Plasmid pNM708B designates the recombinant plasmid with the reverse orientation. In addition, the insertional isomers of plasmids pNM708A and pNM708B are also produced since plasmid pNM702A has two BclI restriction sites for the insertion of the pBR322 fragment. A restriction site map of each of plasmids pNM708A and pNM708B is presented in FIG. 6 of the accompanying drawings.

EXAMPLE 21

Construction of E. coli K12 HB101/pNM708A and E. coli K12 HB101/pNM708B

The desired constructions are made in substantial accordance with the teaching of Example 3 except that plasmid DNA from Example 20B, rather than plasmid pLR2, is used for the transformation. Surviving colonies are first selected, tested for the expected phenotype (Amp$^R$, Tet$^S$) and then conventionally identified as the desired E. coli K12 HB101/pNM708A and E. coli K12 HB101/pNM708B transformants by restriction enzyme and agarose gel electrophoretic analysis of the constitutive plasmids (Wieslander, 1979). The transformant cultures are used for subsequent production and isolation of their respective plasmids.

EXAMPLE 22

Construction of Streptomyces ambofaciens/pNM708A and S. ambofaciens/pNM708B

The desired constructions are made in substantial accordance with the teaching of Example 9 except that DNA from Example 20, rather than plasmids ENM7-02A and pNM702B, is used for the transformation. The resulting transformants are selected for thiostrepton resistance by the method described in Example 9 above. The thus constructed thiostrepton resistant Streptomyces ambofaciens/pNM708A and S. ambofaciens/pNM708B colonies are isolated according to known procedures and then conventionally identified by restriction enzyme and electrophoretic analysis of the constitutive plasmids (Weislander, 1979).

Representative plasmids and transformants constructed in accordance with the foregoing teaching include the following listed in Tables 1 and 2 below.

TABLE 1

Representative Plasmids

| Example No. | Plasmid Name | ~Size in kb | Construction |
|---|---|---|---|
| 23 | pNM709A | 12.4 | Ligation of the ~3.4 kb BamHI neomycin resistance-conferring fragment into plasmid pNM702A at the A site as shown in FIG. 4. Orientation of the ~3.4 kb fragment is the same as in pNM705A. |
| 24 | pNM709B | 12.4 | Reverse orientation of pNM709A. |
| 25 | pNM710A | 11.6 | Ligation of the ~3.4 kb BamHI neomycin resistance-conferring fragment into plasmid pNM703A at the A site as shown in FIG. 5. Orientation of the ~3.4 kb fragment is the same as in pNM706A. |
| 26 | pNM710B | 11.6 | Reverse orientation of pNM710A. |
| 27 | pNM711A | 15.2 | Ligation of the ~2.8 kb SalI erythromycin resistance-conferring fragment provided with BclI linkers into BclI restricted plasmid pNM705A. Orientation of the ~2.8 kb fragment is the same as in pNM707A. |
| 28 | pNM711B | 15.2 | Reverse orientation of pNM711A. |
| 29 | pNM712A | 14.4 | Ligation of the ~2.8 kb SalI erythromycin resistance-conferring fragment provided with BclI linkers into BclI restricted plasmid pNM706A. Orientation of the ~2.8 kb fragment is the same as in pNM707A. |
| 30 | pNM712B | 14.4 | Reverse orientation of pNM712A. |
| 31 | pNM713A | 14.4 | Ligation of the ~5.4 kb BamHI fragment of plasmid pBR325 and the ~9 kb BclI fragment of pNM702B. Insertion and orientation of the ~5.4 kb fragment are the same as in pNM708A. |
| 32 | pNM713B | 14.4 | Reverse orientation of pNM713A. |
| 33 | pNM714A | 17.2 | Ligation of the ~4.8 kb BamHI fragment of plasmid pBR328 and the ~12.4 kb BclI fragment of pNM705A. Insertion and orientation of the ~4.8 kb fragment are the same as in pNM708A. |
| 34 | pNM714B | 17.2 | Reverse orientation of pNM714A. |
| 35 | pNM715A | 17.0 | Ligation of the ~5.4 kb BamHI fragment of plasmid pBR325 and the ~11.6 kb BclI fragment of pNM706A. Orientation of the ~5.4 kb fragment is the same as |

TABLE 1-continued
Representative Plasmids

| Example No. | Plasmid Name | ~ Size in kb | Construction |
|---|---|---|---|
| | | | in pNM708A. |
| 36 | pNM716A | 14.0 | Ligation of the ~4.4 kb BamHI fragment of plasmid pBR322 and the ~9.6 kb BclI fragment of pNM707A. Insertion and orientation of the ~4.4 kb fragment are the same as in pNM708A. |
| 37 | pNM717A | 17.2 | Ligation of the ~4.8 kb BamHI fragment of plasmid pBR328 and the ~12.4 kb BclI fragment of pNM711A. Orientation and insertion of the ~4.8 kb fragment is such that the PstI site is closest to the thiostrepton resistance-conferring fragment. |
| 38 | pNM718A | 20.7 | Same as plasmid pNM717A except that the ~8.3 kb BamHI fragment of plasmid pBR324 is substituted for ~4.8 kb fragment of pBR328. |
| 39 | pNM719A | 10.9 | Ligation of the pEL7 ~9.1 kb XhoI-SacI fragment, provided with BamHI linkers, and the ~1.8 kb BamHI fragment of pLR2. Orientation of the ~1.8 kb fragment is the same as in pNM702A. |
| 40 | pNM719B | 10.9 | Reverse orientation of pNM719A. |
| 41 | pNM720A | 5.55 | Ligation of the pEL7 ~4.75 kb XhoI-BclI fragment, provided with BclI linkers, and the ~.8 kb BclI fragment of pLR2. Orientation of the ~.8 kb fragament is the same as in pNM703A. |
| 42 | pNM720B | 5.55 | Reverse orientation of pNM720A. |

Table 2
Representative Transformants

1. Streptomyces R/R[1] wherein R is *ambofaciens, aureofaciens, griesofuscus, fradiae, lividans, lividans 1326, granuloruber, tenebrarius* or *cinnamonensis* and wherein R[1] independently is plasmid pNM702A, pNM702B, pNM704A, pNM704B, pNM705A, pNM705B, pNM703A, pNM703B, pNM706A, pNM706B, pNM707A, pNM707B, pNM708A, pNM708B or any plasmid listed in Table 1.
2. *E. coli* R[2]/R[3] wherein R[2] is K12 or K12 HB101 and wherein R[3] independently is plasmid pNM708A, pNM708B, pNM713A, pNM713B, pNM714A, pNM714B, pNM715A, pNM716A, pNM716B or pNM718A.

We claim:
1. A functionally independent recombinant DNA cloning vector comprising:
   (a) a functional origin of replication-containing restriction fragment of plasmid pEL7 and
   (b) one or more DNA segments that confer resistance to at least one antibiotic when transformed into a sensitive host cell, said host cell being susceptible to transformation, cell division, and culture.
2. The cloning vector of claim 1 wherein the restriction fragment of pEL7 is the ~6.78 kb BclI restriction fragment.
3. The cloning vector of claim 1 wherein one DNA segment confers antibiotic resistance to thiostrepton.
4. The cloning vector of claim 1 wherein one DNA segment confers antibiotic resistance to neomycin.
5. The cloning vector of claim 1 wherein one DNA segment confers antibiotic resistance to erythromycin.
6. The cloning vector of claim 1 wherein one DNA segment is the ~1.6 kb BamHI or ~0.8 kb BclI restriction fragment of plasmid pLR2.
7. The cloning vector of claim 1 wherein one DNA segment is the ~3.4 kb BamHI restriction fragment of plasmid pLR1.
8. The cloning vector of claim 1 wherein one DNA segment is selected from the group consisting of the ~2.8 kb SalI, ~2.7 kb SalI-BglII, ~3.0 kb HindIII, ~2.5 kb SalI-BamHI, ~2.8 kb XhoI-BglII, and the ~4.1 kb EcoRI-BamHI restriction fragments of plasmid pIJ43.
9. The functionally independent recombinant DNA cloning vector of claim 1 which is selected from the group consisting of plasmids pNM702A, pNM702B, pNM703A, pNM703B, pNM704A, pNM704B, pNM705A, pNM705B, pNM706A, pNM706B, pNM707A, pNM707B, pNM709A, pNM709B, pNM710A, pNM710B, pNM711A, pNM711B, pNM712A, pNM712B, pNM719A, pNM719B, pNM720A and pNM720B.
10. The recombinant DNA cloning vector of claim 9 which is pNM702A.
11. The recombinant DNA cloning vector of claim 9 which is pNM702B.
12. The recombinant DNA cloning vector of claim 9 which is pNM703A.
13. The recombinant DNA cloning vector of claim 9 which is pNM703B.
14. The recombinant DNA cloning vector of claim 9 which is pNM704A.
15. The recombinant DNA cloning vector of claim 9 which is pNM704B.
16. The recombinant DNA cloning vector of claim 9 which is pNM705A.
17. The recombinant DNA cloning vector of claim 9 which is pNM705B.
18. The recombinant DNA cloning vector of claim 9 which is pNM706A.
19. The recombinant DNA cloning vector of claim 9 which is pNM706B.
20. The recombinant DNA cloning vector of claim 9 which is pNM707A.
21. The recombinant DNA cloning vector of claim 9 which is pNM707B.
22. The recombinant DNA cloning vector of claim 9 which is pNM709.
23. The recombinant DNA cloning vector of claim 9 which is pNM710A.
24. The recombinant DNA cloning vector of claim 9 which is pNM712A.

25. The recombinant DNA cloning vector of claim 9 which is pNM719B.

26. The recombinant DNA cloning vector of claim 9 which is pNM720A.

27. A recombinant DNA cloning vector which comprises a replicon that is functional in *E. coli*, a DNA segment that confers antibiotic resistance in *E. coli* and a restriction fragment comprising a recombinant DNA cloning vector of claim 1.

28. The recombinant DNA cloning vector of claim 27 in which the replicon that is functional in *E. coli* and the DNA segment that confers antibiotic resistance in *E. coli* comprise a restriction fragment of a plasmid selected from the group consisting of plasmids pBR322, pBR324, pBR325 and pBR328.

29. The recombinant DNA cloning vector of claim 28 which is pNM708A.

30. The recombinant DNA cloning vector of claim 28 which is pNM713A.

31. The recombinant DNA cloning vector of claim 28 which is pNM714A.

32. The recombinant DNA cloning vector of claim 28 which is pNM717A.

33. A transformed restrictionless Streptomyces host cell comprising a recombinant DNA cloning vector of claim 1.

34. A transformed restrictionless Streptomyces host cell comprising a recombinant DNA cloning vector of claim 9.

35. The transformed host cell of claim 34 which is selected from the group consisting of *Streptomyces ambofaciens, Streptomyces aureofaciens, Streptomyces griseofuscus, Streptomyces fradiae, Streptomyces lividans, Streptomyces granuloruber, Streptomyces tenebrarius,* and *Streptomyces cinnamonensis*.

36. The transformed host cell of claim 35 which is *Streptomyces ambofaciens*/pNM702A.

37. The transformed host cell of claim 35 which is *Streptomyces ambofaciens*/pNM705A.

38. The transformed host cell of claim 35 which is *Streptomyces ambofaciens*/pNM707A.

39. The transformed host cell of claim 35 which is *Streptomyces ambofaciens*/pNM703A.

40. The transformed host cell of claim 35 which is *Streptomyces lividans* 1326/pNM703A.

41. The transferred host cell of claim 35 which is *Streptomyces ambofaciens*/pNM719A.

42. The transformed host cell of claim 35 which is *Streptomyces ambofaciens*/pNM720A.

43. A transformed host cell selected from the group consisting of restrictionless Streptomyces and *E. coli*, said hose cell comprising a recombinant DNA cloning vector of claim 27.

44. A transformed host cell selected from the group consisting of restrictionless Streptomyces and *E. coli*, said host cell comprising a recombinant DNA cloning vector of claim 28.

45. The transformed host cell of claim 43 which is *E. coli*.

46. The transformed host cell of claim 44 which is *E. coli* K12 HB101/pNM708A.

47. The transformed host cell of claim 44 which is *E. coli* K12 HB101/pNM713A.

48. The transformed host cell of claim 44 which is *E. coli* K12 HB101/pNM717A.

49. The 6.78 kb BclI restriction fragment of claim 2.

* * * * *